(12) United States Patent
Lorsch

(10) Patent No.: US 8,121,855 B2
(45) Date of Patent: *Feb. 21, 2012

(54) METHOD AND SYSTEM FOR PROVIDING ONLINE MEDICAL RECORDS

(75) Inventor: Robert H. Lorsch, Beverly Hills, CA (US)

(73) Assignee: MyMedicalRecords.com, Inc., Los Angeles, CA (US)

( * ) Notice: Subject to any disclaimer, the term of this patent is extended or adjusted under 35 U.S.C. 154(b) by 1753 days.

This patent is subject to a terminal disclaimer.

(21) Appl. No.: 11/225,518

(22) Filed: Sep. 12, 2005

(65) Prior Publication Data

US 2007/0061169 A1    Mar. 15, 2007

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .............................. 705/2; 705/3
(58) Field of Classification Search ............. 705/2–3
See application file for complete search history.

(56) References Cited

U.S. PATENT DOCUMENTS

| | | |
|---|---|---|
| 5,404,292 A | 4/1995 | Hendrickson |
| 5,499,293 A | 3/1996 | Behram et al. |
| 5,778,882 A | 7/1998 | Raymond et al. |
| 5,924,074 A | 7/1999 | Evans |
| 5,926,526 A | 7/1999 | Rapaport et al. |
| 5,970,463 A | 10/1999 | Cave et al. |
| 5,974,124 A | 10/1999 | Schlueter, Jr. et al. |
| 5,997,476 A | 12/1999 | Brown |
| 6,000,828 A | 12/1999 | Leet |
| 6,032,199 A | 2/2000 | Lim et al. |
| 6,073,106 A * | 6/2000 | Rozen et al. ............ 705/3 |

(Continued)

FOREIGN PATENT DOCUMENTS

EP    0 764 911 A1    3/1997

(Continued)

OTHER PUBLICATIONS www.linxcom.com, Jan. 7, 2005, Obtained from Internet Archive Wayback Machine (www.archive.org), linxconnect.htm, linxconnect_faq.htm.*

(Continued)

*Primary Examiner* — Robert Morgan
*Assistant Examiner* — Joy Chng
(74) *Attorney, Agent, or Firm* — McKee, Voorhees & Sease, PLC

(57) ABSTRACT

A method for providing a consumer with the ability to access and collect personal health records associated with the consumer in a secure and private manner is provided. The method includes assigning a toll-free phone number individually associated with and dedicated to the consumer for private fax and voice communications from a health care provider, associating access information with the consumer for the consumer to use to access a secure web site, receiving a private fax communication comprising a personal health record associated with the consumer for which the consumer has requested and given permission to the health care provider to send to the toll-free number, converting the private fax communications into an image file format, storing the health record encoded in the image file format, and providing the consumer with secure access to the web site using the access information and providing on the web site an interface to the health records of the consumer for the consumer to access the health record.

25 Claims, 9 Drawing Sheets

U.S. PATENT DOCUMENTS

| | | | | |
|---|---|---|---|---|
| 6,082,776 | A * | 7/2000 | Feinberg | 283/72 |
| 6,088,677 | A | 7/2000 | Spurgeon | |
| 6,223,559 | B1 | 5/2001 | Coleman | |
| 6,463,417 | B1 | 10/2002 | Schoenberg | |
| 6,574,484 | B1 | 6/2003 | Carley | |
| 6,725,200 | B1 | 4/2004 | Rost | |
| 6,738,784 | B1 | 5/2004 | Howes | |
| 6,845,448 | B1 | 1/2005 | Chaganti et al. | |
| 6,871,214 | B2 * | 3/2005 | Parsons et al. | 709/206 |
| 6,941,271 | B1 | 9/2005 | Soong | |
| 6,988,075 | B1 * | 1/2006 | Hacker | 705/3 |
| 7,257,967 | B2 | 8/2007 | Rheinstein | |
| 7,306,560 | B2 | 12/2007 | Iliff | |
| 2001/0041991 | A1 * | 11/2001 | Segal et al. | 705/3 |
| 2002/0046061 | A1 | 4/2002 | Wright et al. | |
| 2002/0059587 | A1 * | 5/2002 | Cofano et al. | 725/35 |
| 2002/0077861 | A1 | 6/2002 | Hogan | |
| 2002/0103675 | A1 | 8/2002 | Vanelli | |
| 2002/0120470 | A1 | 8/2002 | Trice, Sr. | |
| 2002/0128865 | A1 | 9/2002 | Alten | |
| 2002/0178631 | A1 | 12/2002 | Morton | |
| 2002/0189146 | A1 | 12/2002 | Lyon | |
| 2003/0014282 | A1 | 1/2003 | Haaksma et al. | |
| 2003/0037065 | A1 | 2/2003 | Svab | |
| 2003/0040940 | A1 | 2/2003 | Nehammer | |
| 2003/0059751 | A1 | 3/2003 | Welles | |
| 2003/0086591 | A1 | 5/2003 | Simon | |
| 2003/0098356 | A1 | 5/2003 | Gombar | |
| 2003/0132132 | A1 | 7/2003 | Small | |
| 2003/0140044 | A1 * | 7/2003 | Mok et al. | 707/10 |
| 2003/0208382 | A1 | 11/2003 | Westfall | |
| 2003/0226889 | A1 | 12/2003 | Morrison, Jr. | |
| 2003/0229452 | A1 | 12/2003 | Lewis et al. | |
| 2003/0233844 | A1 | 12/2003 | Rheinstein | |
| 2004/0078229 | A1 | 4/2004 | Gay et al. | |
| 2004/0228336 | A1 * | 11/2004 | Kung et al. | 370/352 |
| 2004/0267572 | A1 | 12/2004 | Emery et al. | |
| 2005/0165285 | A1 | 7/2005 | Iliff | |
| 2005/0209891 | A1 | 9/2005 | Jacobus et al. | |
| 2005/0251423 | A1 | 11/2005 | Bellam et al. | |
| 2006/0004588 | A1 | 1/2006 | Ananda | |
| 2007/0061170 | A1 | 3/2007 | Lorsch | |
| 2009/0007237 | A1 | 1/2009 | Lorsch | |
| 2009/0055894 | A1 | 2/2009 | Lorsch | |

FOREIGN PATENT DOCUMENTS

| | | |
|---|---|---|
| JP | 9-218902 | 8/1997 |
| JP | 2001-350847 | 12/2001 |

OTHER PUBLICATIONS

MyMedicalRecords.com, Inc., Examiner's Report from Australian Patent Application No. 2006202057, dated Jul. 31, 2007, 2 pages.

http://web.archive.org/web/20050909014053/http://www.mbox.com.au, "mBox—Unified Messaging", printed off of Internet Aug. 11, 2009, 1 page.

mymedicalrecords.com, Inc., PCT/US06/04867, Notification of Transmittal of International Preliminary Examination Report dated May 17, 2010.

* cited by examiner

METHOD AND SYSTEM FOR PROVIDING ONLINE MEDICAL RECORDS

BACKGROUND OF THE INVENTION

The present invention relates to the provision of online medical records. More particularly, the present invention relates to providing a means for consumers to request their medical records from health care providers, store the medical records, and provide for private communications between the consumers and their health care providers.

Medical and other health information can be particularly sensitive communications. Laws such as the HIPPA Privacy Rule restrict, limit, or place specific conditions on the dissemination of medical records. Laws such as the Health Insurance Portability and Accountability Act (HIPAA) provide a patient with the right to access to their own medical records.

A health provider, such as a hospital may require a patient to submit to their own privacy practices as a condition for treatment or admittance. A privacy practice statement of the health provider will likely explain that the patient the right to inspect and copy their medical records, but there may be significant procedural hurdles to overcome that burden both the health provider and the patient. For example, the patient would be required to provide a written request, there may be processing delays in receiving copies of the medical or health related records, and additional processing charges resulting from the inconvenience created for the health provider to comply with the procedural hurdles that they put in place to avoid inappropriately disclosing records of their patients.

Of course, privacy concerns regarding a patient's medical records creates other problems for health care providers. For example, suppose a health care provider needs to communicate with a patient over the phone to check on a patient, request additional information regarding a patient's current condition, to schedule a test, report the results of a test, express the need for a return visit, or for other reasons related to providing health care to the patient. The health care provider calls the patient at home or at work and the patient is not available. Instead, the phone is answered by another person who could be a co-worker or family member. Alternatively, the health care provider is provided with the opportunity to leave a voicemail message. The health care provider must be very cautious to avoid inadvertently disclosing private information. Thus, the health care provider may not be able to leave a message with another person or with a voicemail system if doing so would violate the patient's privacy rights or expectations of privacy. Even in cases where the health care provider may be legally authorized to do so via a previously agreed upon privacy policy, doing so may be against the person's wishes as they did not understand what they were consenting to when they consented to the privacy policy or did not understand their rights under the privacy policy. A message for the patient may provide other parties with more information then the patient would want them to know. Even when a health care provider attempts to leave a seemingly innocuous message with a voicemail system or with another individual, more information may be shared then the patient wants to be shared. For example, a message left with another requesting that the patient call a particular doctor may be more than what the patient would want shared with others. For example, suppose it is known or readily determined that the doctor is an obstetrician and the patient is a woman who does not want her significant other to know she is pregnant yet. Suppose it is known or readily determined that the doctor is an oncologist and the patient does not want their co-workers or employer to know that the patient has cancer. Mere knowledge of the doctor's name, in these cases would be sufficient to make an educated guess about the patient's condition or potential condition. A patient may consider this a violation of their privacy. Regardless of whether or not the patient has any legal recourse, this can result in the patient being upset and can have a negative impact on the relationship between the patient and their health care provider.

Of course, instead of leaving a message, a health care provider could simply call back, but this is inconvenient for the health care provider or their staff and may unduly delay the amount of time before the patient receives the message. Thus, private and secure communications would benefit both the health care provider and the patient. The health care provider would not have to worry about disclosing private information to a party who should not have the information. And, the patient would be more likely to receive the communications sooner and could take comfort knowing that their privacy was maintained.

Another problem relating to medical records is that where an individual sees multiple health care providers, the inconvenience of requesting medical records is multiplied. Given the inconvenience and the potential delay in obtaining records it is also likely that in such instances the individual does not actually compile a complete medical history. To the extent the individual has their records, the individual must determine a method of storing and organizing them.

Yet another problem relating to medical records is that often times they are most needed at a time when the individual is unable to provide them. For example, in emergency situations it would be desirable for caregivers to know and understand the individual's medical history. Knowledge of specific allergies may be essential to avoid administration of medications that would adversely impact the condition of the individual. Knowledge of pre-existing conditions may be essential to correct diagnosis and treatment. What is desired is a way that relevant medical records could be shared when needed most.

Various attempts have been made to assist consumers with their medical records in different ways. One example of such an attempt is Synchart. Synchart is a web-based service (www.synchart.com) that allows consumers to enter their personal and family health information into a database. Users can enter doctor visits, immunizations, hospital visits, allergies, and other relevant information and generate reports based on the data entered. As part of the services, consumers receive a CD with their medical information data, as well as a wallet card. Because medical data is stored on the Synchart web server, user health information is accessible from any Internet-connected computer, which Synchart claims will allow doctors and other providers to access user information if the user gives them account information.

One of the problems with a service such as Synchart is that it requires users to enter information about their health histories into a database, a time consuming and cumbersome process which is inconvenient and sometimes difficult. These issues are further magnified if an individual does not have a complete understanding of their medical records. Another problem of such a system is that clerical errors by the user can result in inaccurate information. A further problem is that medical information is not immediately available if the individual does not immediately enter the information. Such a problem is exacerbated by the fact that often times when an individual is frequently seeing health care providers they are ill or injured and it is particularly inconvenient to update their medical records. Finally, such a system does not address issues of obtaining the medical records from the health care provider.

Redi-Records is another example of a system that assists consumers with obtaining access to their medical records. For a fee, Redi-Records will gather all of a subscriber's medical records from different doctors and hospitals. Once the records are gathered, Redi-Records will digitize them and put them onto two mini-CDs. Users can carry 1 mini-CD in their wallet and keep one at home. For an additional cost, the company will update a user's records every 180 or 90 days. Such a service is marketed with the promise that having records on a mini-CD will make it easier for you to receive proper treatment in the event of a medical emergency. One of the problems with such an approach is that the records are not necessarily current. Another problem with such an approach is that a third party is involved so that complex forms will need to be completed by the consumer and the consumer's providers in order to grant the third party access to the medical records which could cause delay in gathering information. Due to the third party involvement, there is a chain of human handling of the documents that could compromise the privacy of the documents. In addition, as the mini-CDs may not be secured or password protected, or the information about how to access them readily available. Where the mini-CDs are not secured or password protected, unauthorized individuals could access a person's medical records.

Another prior art approach is HeartRecord (www.heartcenteronline.com). This services focuses on cardiac patients. Users pay a subscription fee and are able to enter information about their medical history, doctors, and prescriptions into a database that is accessible using the Internet with a secured password. As a result, important information is available in the event of a medical emergency or when users visit a doctor. HeartRecord also allows users to upload their EKGs and other vital images to their account either from a computer, or by e-mailing, faxing or mailing the image to the company. HeartRecord has several inherent problems. HeartRecord's system places the onus of entering data and uploading images completely on the user. Another problem with such as service is that it is limited in scope. A further problem with such as system is that it does not create a private communications link between a doctor and patient.

Another prior art approach is demonstrated by Personal MD. This product (www.personalmd.com) uses a fax-based technology to allow users to store records that can be accessed via the Internet. Personal MD also offers a feature where users can file the most critical information in a folder marked "Emergency", which can be printed out by personnel via fax in the event of a medical crisis. PersonalMD also offers medication reminders and other calendar features, and the site includes syndicated health information content. One of the problems with this approach is ease of use. For example with Personal MD, a non-dedicated number is used thus the person sending a fax must enter a PIN before sending the fax. This can create an unacceptable inconvenience for a busy doctor's office and can cause frustration. Moreover, it also creates an additional opportunity for human error in that use of the wrong pin number may direct the fax to a wrong destination. Such a system is not focused on providing a private communications link between a patient and their health care provider.

Another prior art approach is Web MD Health Manager offered by WebMD (www.webmd.com). This system allows users to enter data about their personal health such as health conditions, blood pressure, cholesterol level and other metrics. This system will then run those numbers against a database to provide a personal "self-assessment" and provide tips on better health. Such a system does not provide for storage of medical records or a private communications links between a health care provider and patient.

Another prior art approach is available from iHealthRecord.org. This service provides an interactive data entry screen that allows users to enter their personal and family health histories. This information can then be printed out on a wallet card. One of the problems with such an approach is that it requires users to enter information on their medical records into a database, a time consuming and cumbersome task which can also result in inaccuracies. In addition, this approach does not provide a secure communications link between a health care provider and their patient or offer storage and management of personal health and medical records.

Thus, despite the advancements in these areas, problems remain. In particular, there is a general lack of recognition of the need to provide secure and private communications between a health care provider and their patient and to do so in a manner that is convenient to both the health care provider and the patient. There is also a general lack of recognition of the problems for an individual to exercise their rights to receive access to their health care records and be able to store and maintain those records in one secured, password protected account that allows for files to be categorized, annotated, sorted and viewed based on date, type of record, doctor, or user.

BRIEF SUMMARY OF THE INVENTION

Therefore it is a primary object, feature, or advantage of the present invention to improve upon the state of the art.

It is a further object, feature, or advantage of the present invention to facilitate health care personnel's compliance with HIPAA or other legal requirements regarding privacy of medical records.

A still further object, feature, or advantage of the present invention is to provide meaningful access to health care records by an individual thereby allowing the individual to exercise their legal rights with respect to controlling access to their medical records.

Yet another object, feature, or advantage of the present invention is provide individuals with immediate access to health care records in emergency situations to assist in providing appropriate care.

A further object, feature, or advantage of the present invention is to provide a convenient and cost effective method for health care providers to comply with laws regarding privacy of health care records.

A still further object, feature, or advantage of the present invention is to provide a convenient and cost effective method for individuals to request that their health care providers provide copies of medical records.

Another object, feature, or advantage of the present invention is to provide a private communications link between health care personnel and their patients.

Yet another object, feature, or advantage of the present invention is to provide for placing an individual in control of their medical records and allowing them to selectively provide access to others.

A still further object, feature, or advantage of the present invention is to facilitate storing all of an individual or family's medical records and related information in a single location so that health care personnel can be given complete medical information/history when needed or analysis can be performed on the medical records.

Another object, feature, or advantage of the present invention is to provide a means for individuals to create calendars to remind them of the need to refill prescriptions.

Yet another object, feature, or advantage of the present invention is to provide a means for individuals to create calendars to maintain doctor's appointments.

A further object, feature, or advantage of the present invention is to provide reminder messages regarding the need to refill prescriptions or remember doctor's appointments.

A still further object, feature, or advantage of the present invention is to provide a method to store, organize, and annotate medical records and also to customize the storage by giving the user the ability to name the folders in which those records are stored.

Another object, feature, or advantage of the present invention is to give users the ability to upload images, such as x-rays or scans.

Yet another object, feature, or advantage of the present invention is to give users the ability to forward records via fax to a health care provider.

A further object, feature, or advantage of the present invention is to give users the ability to see if there are any possible interactions between prescription drugs they are taking.

One or more of these and/or other objects, features, or advantages of the present invention will become apparent from the specification and claims that follow.

According to one aspect of the present invention, a method for providing a consumer with the ability to access and collect personal health records associated with the consumer in a secure and private manner is provided. The method includes assigning a toll-free phone number individually associated with and dedicated to the consumer for private fax and voice communications from a health care provider. Next, the method provides for associating access information with the consumer for the consumer to use to access a secure web site. The method also provides for receiving a private fax communication comprising a personal health record associated with the consumer for which the consumer has requested and given permission to the health care provider to send to the toll-free number, converting the private fax communications into an image file format (such as PDF), and storing the health record encoded in the image file format. The method also provides for providing the consumer with secure access to the web site using the access information and providing on the web site an interface to the health records of the consumer for the consumer to access the health record.

According to another aspect of the present invention, a kit is provided for assisting a customer with exercising rights to medical records associated with the customer, accessing the health records, maintaining the medical records as private, and providing access to the health records in case of emergency. The kit includes an access card and at least one document such as a sticker. The access card includes access information associated with the customer to be used to access a secure web site providing access to health records of the customer to be used to convey the access information to another in event of a medical emergency associated with the customer. The document or sticker includes a request to a health care provider to electronically send the medical records to a destination and granting permission by the customer to the health care provide to electronically send the medical records to the destination and wherein the medical records sent to the destination are accessible on the secure web site.

According to another aspect of the present invention, a system for communicating personal health records of a consumer is provided. The system includes a consent document, a fax server, and a web server. The consent document, preferably a sticker, provides instructions for and giving permission to a health care provider to fax health records of the consumer to a dedicated phone number associated with the consumer. The fax server is for receiving faxes of the health records directed to the dedicated phone number. The web server is in operative communication with the fax server and adapted to provide a secure web-based interface to the health records. The web-based interface provides the ability to upload images through a web browser, allow a user to send faxes to health care providers, and perform other functions associated with managing their health care records.

DETAILED DESCRIPTION OF THE PREFERRED EMBODIMENT

The present invention provides for a convenient method for individuals to collect and store their private medical information and to provide private communications between the individual and their health care providers. One of the ways that the present invention collects and stores private medical information and facilitates private communications is through use of a LIFELINE which is a dedicated toll-free number for fax and voice communications. This dedicated toll-free number provides direct and private communications between a health care provider and their patient so that a health care provider can be assured that they are maintaining patient communications in secret and to avoid violating applicable privacy laws or patient expectations regarding privacy.

Figure 1:
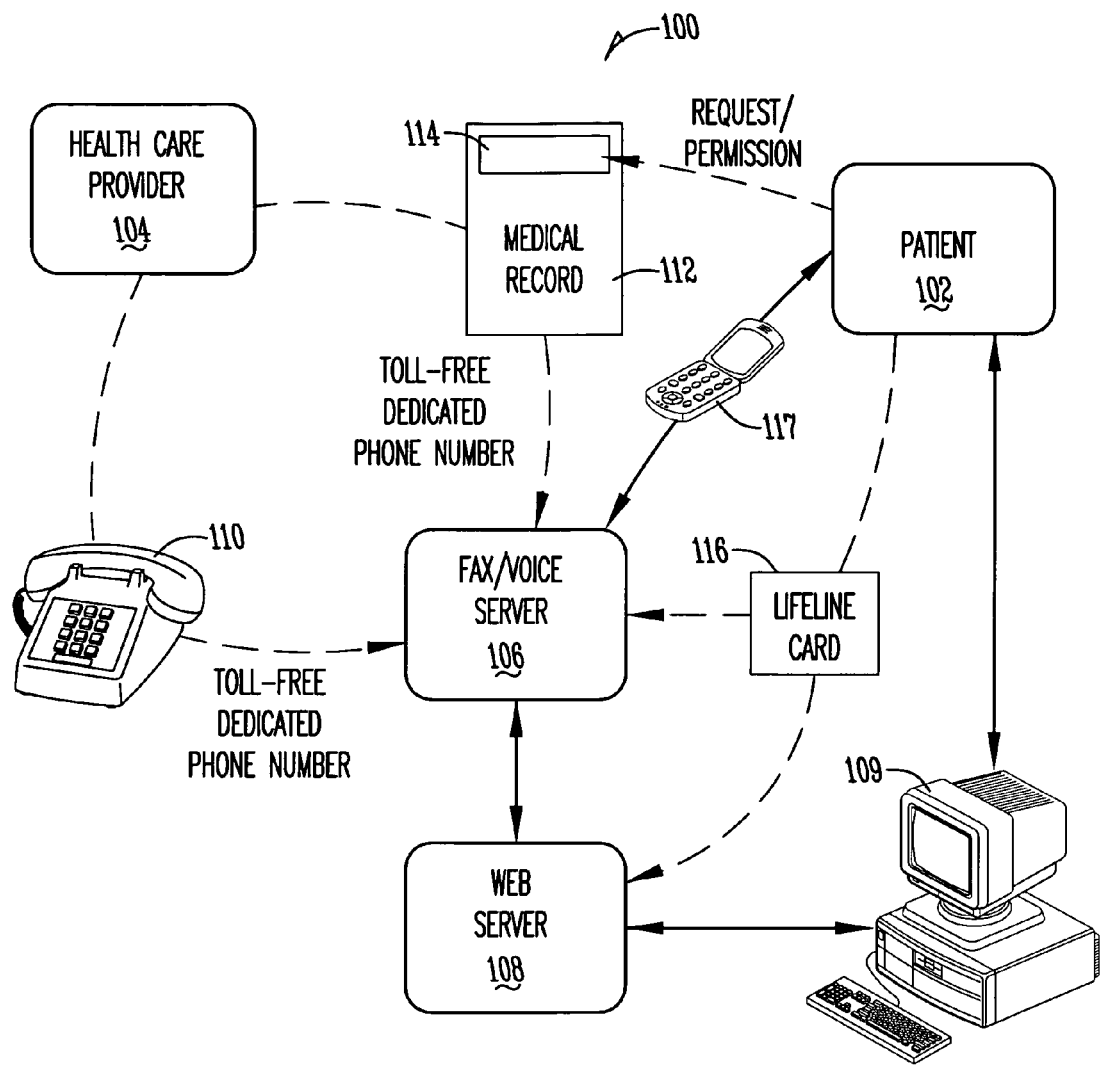
FIG. 1 is diagram illustrating one embodiment of a system of the present invention.

FIG. 1 is a diagram illustrating one embodiment of a system 100 of the present invention. In FIG. 1, a consumer or patient 102 is shown. A health care provider 104 is also shown as well as a fax/voice server 106. A web server 108 is operatively connected to the fax/voice server 106. The health care provider 104 uses the phone 110 to communicate private voicemail messages through a toll-free dedicated phone number to the fax/voice server 106. In addition, the health care provider faxes health or medical records 112 to the fax/voice server 106 using the toll-free dedicated phone number. The medical record 112 preferably has a sticker 114 present on the medical record 112. The sticker 114 indicates or instructs the health care provider or their staff to fax the information to the toll-free dedicated phone number. In addition, the sticker 114 provides an indication of clear consent from the patient to the health care provider 104 to the toll-free dedicated phone number. Thus, it becomes a simple process for a consumer or patient 102 to provide their health care provider 104 with instructions to fax health records, a simple process for the health care provider to obtain permission to fulfill a request for health care records, and a simple process for the health care provider to do so in a secure and convenient manner as the fax is going directly to a toll-free dedicated phone number associated with the patient.

The web server 108 is operatively connected to the fax/voice server 106 such as over a network or otherwise. A patient 102 or their proxy can communicate directly with the web server 108 through a computing device 109 or the fax/voice server 106 using a phone 117. The patient 102 can use a LIFELINE card 116 that contains access information to log on to the web server 108 associated with a web site of the present invention, or as a reminder of their tollfree dedicated phone number which they can call to access voicemail messages, listen to text-to-speech conversion of emails, or otherwise access information.

The present invention also allows a patient 102 to upload files using a computing device 109 to the web server 108. In addition, the patient 102 can use the computing device 109 to interact with the web server 108 to specify that a prescription or other personal health record is faxed via the fax/voice server 106 to a health care provider 104.

Figure 2:
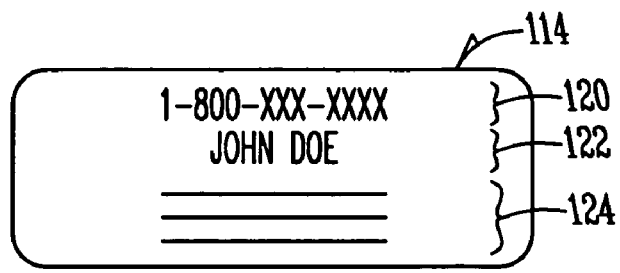
FIG. 2 is a pictorial representation of a sticker authorizing transmissions of records to the user account according to one embodiment of the present invention.

FIG. 2 illustrates one embodiment of a sticker 114 for a patient to give to their healthcare provider to request or instruct their health care provider to fax medical records to the tollfree dedicated phone number associated with the patient. Although it is preferred that a sticker 114 be used because of the added convenience provided by being able to permanently or semi-permanently attach to a paper medical record, the present invention contemplates that other types of documents could be used. The sticker 114 includes the LIFELINE phone number 120 which is the tollfree dedicated phone number associated with the patient. Note that there is no pin number required which greatly simplifies the process of faxing documents. In addition, the name 122 of the patient is shown. There is also a written request 124 on the sticker 114 that instructs the health care provider to fax the records and explicitly gives permission to fax the health care record. The language of the written request may vary as necessary to comply with any applicable laws. It should be appreciated that the sticker 114 provides great convenience to both an individual who wants to instruct their health care provider to give them access to their medical records as well as to the health care provider who can now easily provide the individual with access to their medical records. The present invention further contemplates that medical alert information can also be placed on the sticker 114. The types of medical alert information includes, without limitation, blood type information (i.e. ABO and Rhesus information), allergies to drugs, presence of a pacemaker, diabetes, epilepsy, or other conditions.

Figure 3A:
FIG. 3A and FIG. 3B illustrate a card with medical record access information according to one embodiment of the present invention.
Figure 3B:
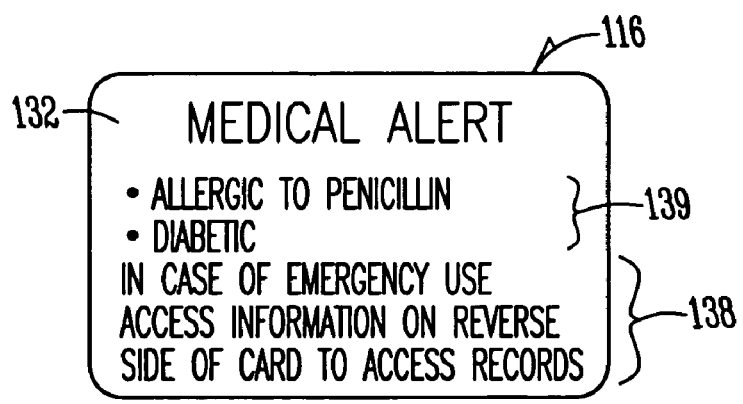

FIG. 3A and FIG. 3B illustrate one embodiment of a LIFELINE card 116. The LIFELINE card has a front side 130 and an opposite back side 132. The card 116 includes the name of the individual 122, a URL for a web site 136 which stores medical records for the individual. In addition there is access information 134 such a username and password. The card 116 also includes the tollfree dedicated phone number 120 associated with the individual. On the back side 132 of the card 116 as best shown in FIG. 3B, medical alert information 139 is provided. The medical alert information 139 can include allergies which the individual has, medical conditions such as diabetes or epilepsy, the presence of a pacemaker, or other medical information that may be of great importance in evaluating or treating the individual in the case of a medical emergency. The medical alert information can further include blood type information (i.e. ABO and Rhesus information). Also, instructions 138 are provided on the card 116 to indicate how one could access complete medical records or information about the individual.

The present invention contemplates including the sticker 114 (or other permission/request document) and the LIFELINE card 116 in a welcome kit when an individual or family subscribes or signs-up for the service. In addition, from the web site associated with the service, preferably addition stickers and/or additional cards can be printed and information can be updated as necessary.

Figure 4:
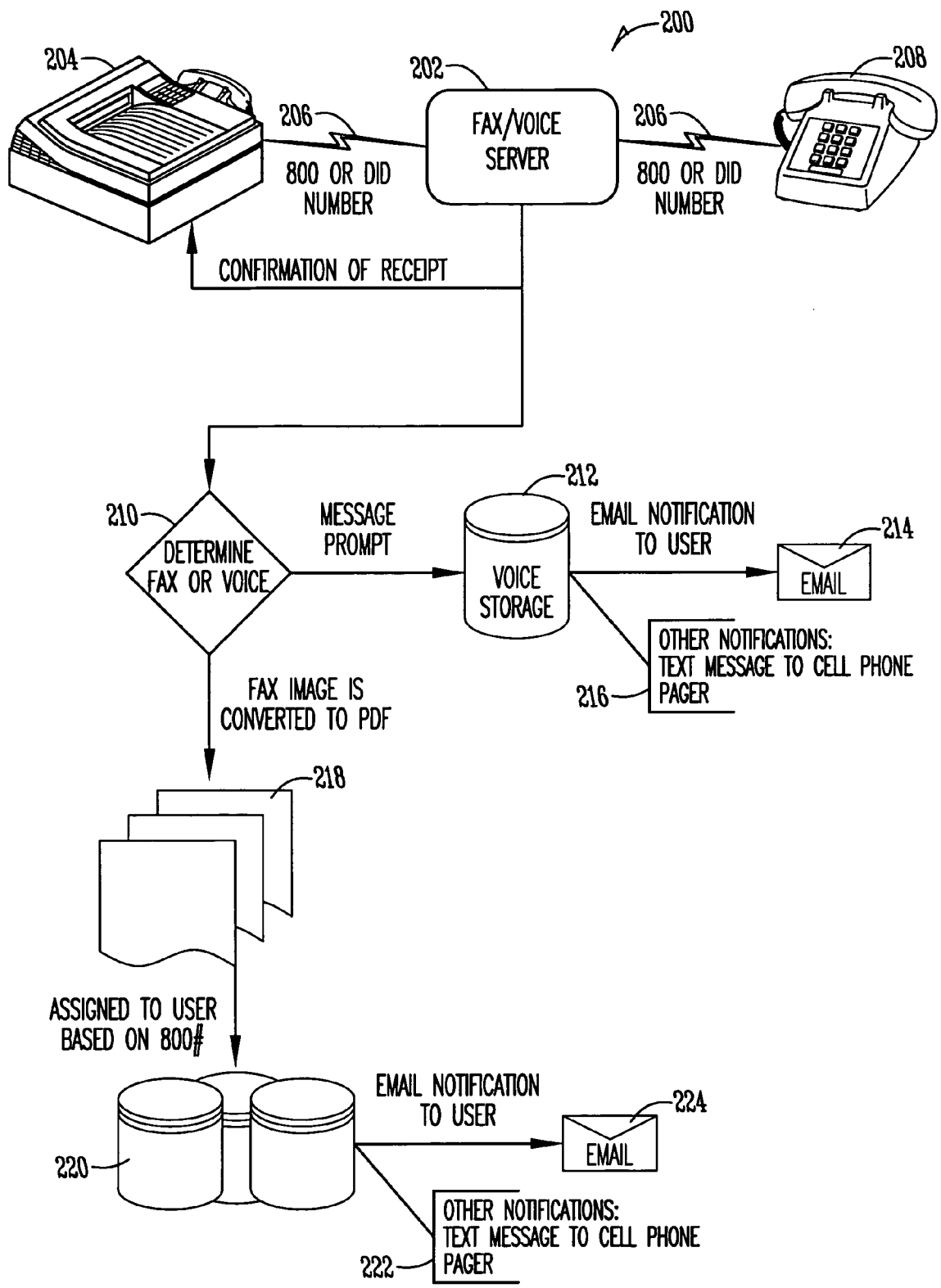
FIG. 4 is a diagram illustrating one embodiment of a system of the present invention.

FIG. 4 illustrates one embodiment of a system of the present invention. Preferably such a system is implemented using equipment from Prairie Systems, Inc. of Omaha, Nebr., although the present invention contemplates that other vendors may be used. As shown in FIG. 4, the system 200 includes a fax/voice server 202. The fax/voice server 202 is accessible by a fax machine 204 or a phone 208 through using a dedicated phone number. Preferably, the phone number 206 is toll-free as this increases the accessibility and convenience of the system which is very important. However, the phone number could also be a direct dial phone number. When the fax/voice server 202 receives a call, determination is made in step 210 as to whether the call is a voice call or a fax call. Where the call is a voice call, an interactive voice response (IVR) system is used to determine who the caller is, the purpose of the call, or other information, and then stores any voicemail message in voice storage 212. The system is adapted notify the individual that there is a voicemail message through an email notification in step 214 and/or other types of notification in step 216. Other types of notification can include, but are not limited to text messages to a cell phone or pager. Thus, a health care provider can call the LIFELINE number 206 and leave a voicemail message for the individual and know that the communication is a private communication. Thus, the health care provider can leave private and confidential information, such as the results of a test, or the need to schedule a new appointment, or other information. The individual is alerted to the presence of the voicemail message and can then call-in to the fax/voice server to check messages.

Where documents are faxed, fax images are collected and converted to portable document format (PDF) documents 218. Although, the PDF format is preferred, the present invention contemplates that other types of document conversions can be done as may be appropriate in a particular implementation of the present invention. Based on the dedicated phone number used to send the documents, the faxed documents are assigned to a user account and stored in step 220. The individual is alerted via email that the documents have been sent in step 224. Alternatively, the individual is alerted via text messaging in step 222 that a fax has been sent.

Figure 5A:
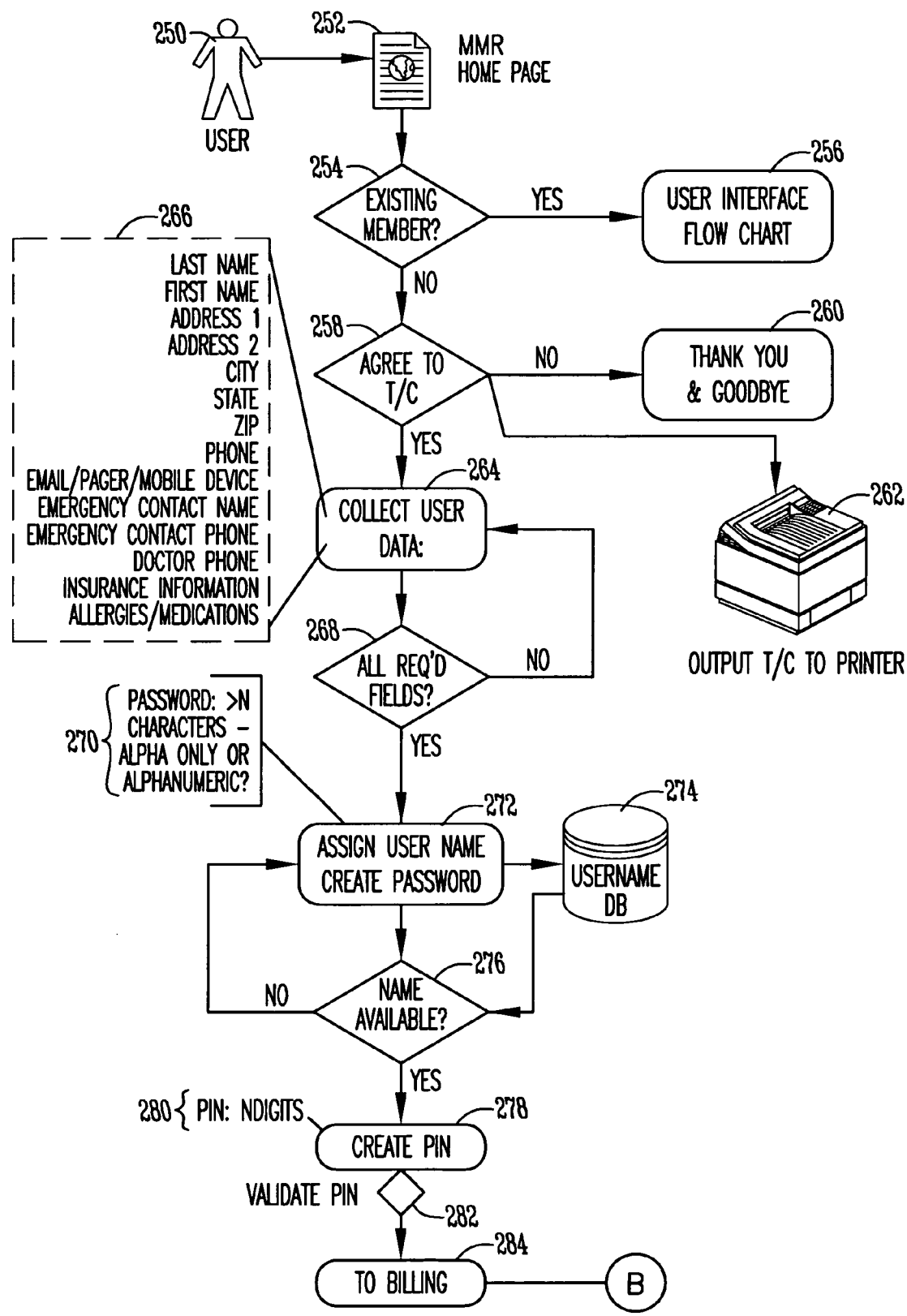
FIG. 5A and FIG. 5B are flow diagrams illustrating an enrollment process according to one embodiment of the present invention.
Figure 5B:
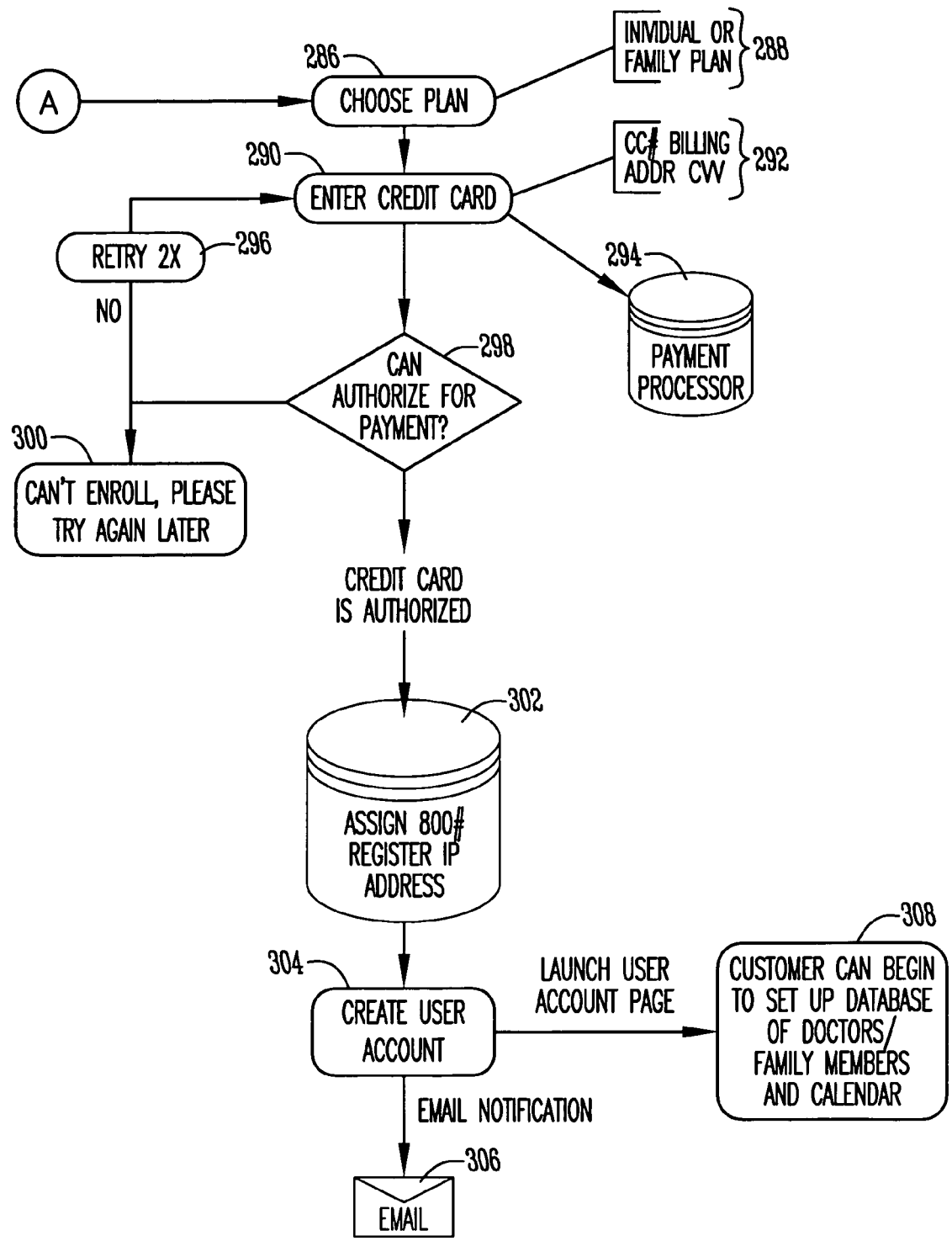
Figure 6:
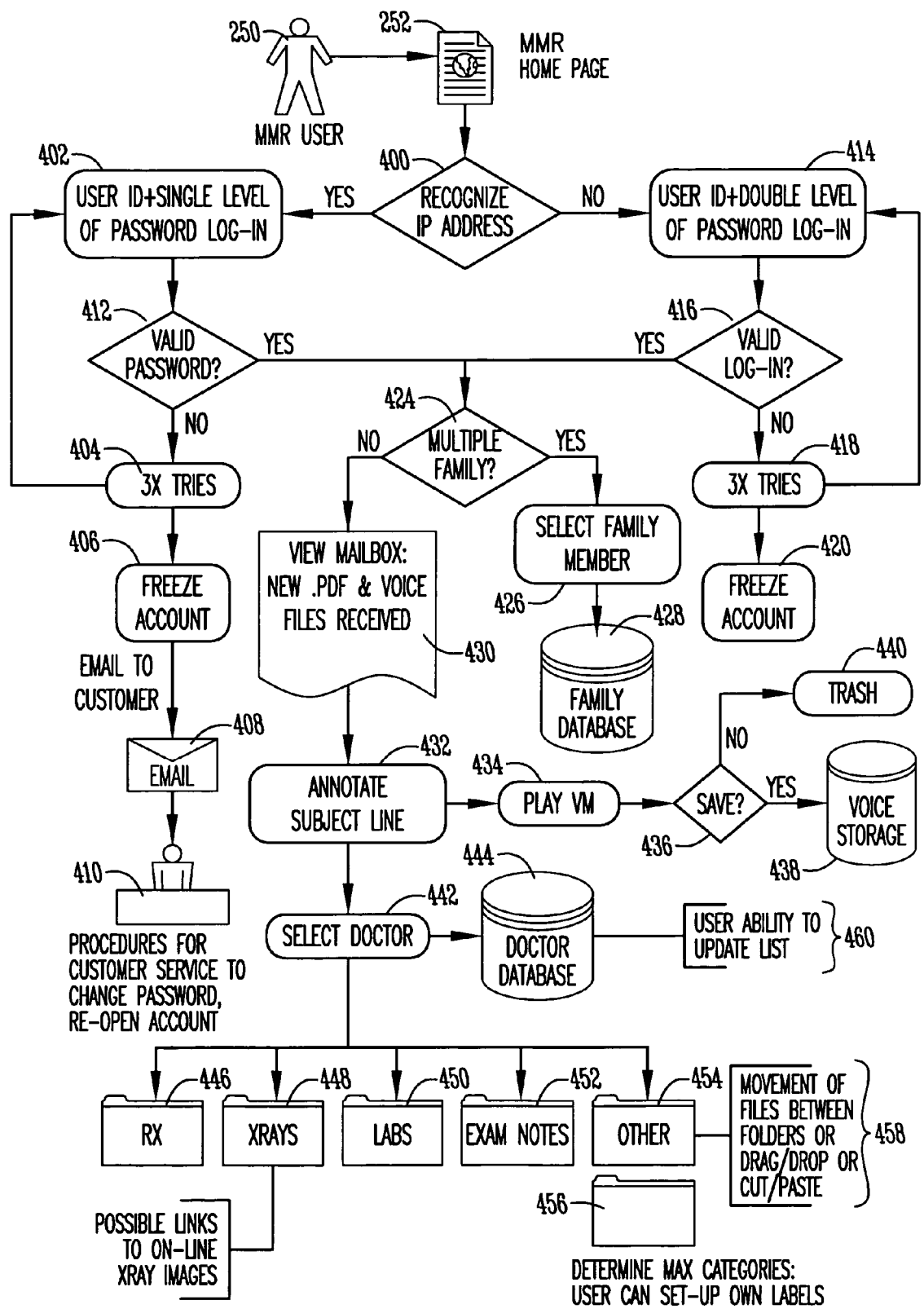
FIG. 6 is a flow diagram for accessing records according to one embodiment of the present invention.

The web site of the present invention provides a convenient location to collect and store health care records and provide secure access to the records. It also provides a convenient way to enroll in a service for providing online access to health records. FIGS. 5A and 5B provides one embodiment of an enrollment process In FIG. 5A, a user 250 accesses a home page 252 for a medical records web site. In step 254, a determination is made as to whether the user 250 is an existing member. If the member is, then in step 256 the user is provided access to their user interface as shown in FIG. 6. If not, then in step 258 a determination is made as to whether the user 250 agrees to terms and conditions of service. If not, then in step 260 the user is thanked for their interest but not allowed to continue. The user is also given the option or encouraged to output the terms and conditions to a printer in step 262 so that they can review them closely and maintain a copy for their records if they wish. If in step 260, the user agrees to the terms and conditions of service then in step 264 the system collects user data. User data 266 can include last name, first name, address information, city, state, zip code, phone number, email/pager/mobile device information, emergency contact name, emergency contact phone number, primary care physician phone number, insurance information, allergies and medications, and/or other information. If all fields are received in step 268, then in step 272 the system assigns a user name and password. It is to be understood that the user may also request a particular username and/or set their own password. Where a user selects their own password, then in step 270, a determination is made as to whether the password meets security requirements. For example, there may be a minimum number of characters required, or there must be at least one numeric character, or other requirements. Where the user is allowed to select their own name, in step 274, a username database is searched and in step 276 a determination is made as to whether or not the name is available. If it is, then in 278 the user is permitted to create a personal identification number (PIN). In step 280, a rule such as one requiring a particular number of digits or a particular minimum digits is applied. In step 282 the PIN is validated and the enrollment process proceeds to billing options in step 284. In FIG. 5B, the user is allowed to choose a plan in step 286. The individual could, for example, choose an individual or family plan from the plan options 288. In step 290, the user enters credit card information 292 which may include a credit card number, billing address, and CVV number. This information is then submitted to a payment processor 294. In step 298, a determination is made as to whether the credit card information can be authorized for payment. If not, then the number of retries is determined in step 296 and the user is allowed to re-enter their credit card information in step 290. If there have already been two tries to validate credit card information, then in step 300 the individual is told that they can not enroll at this time and should try again later. If payment is authorized in step 298 then in step 302 a dedicated tollfree phone number is assigned and an IP address associated with the user is registered. In step 304 a user account is created. In step 306 an email notification confirming registration is sent to the user. In step 308 the user can begin to setup their personal web site such as their database of doctors, family members, calendar, and otherwise configure their web site.

After registration, the user can access the user interface of the web site. FIG. 6 illustrates one embodiment of the user interface 256. The user 250 can access the homepage 252. In step 400, a determination is made as to whether the system recognizes the ip address being used by the user as being associated with the user. If the ip address is not recognized then extra security measures are taken beginning in step 414. In step 414 a username and a double level of password log-in is required. If a valid log-in 416 then the process proceeds to step 424. If not, then in step 418, the number of invalid log-in attempts or tries is monitored and if it is three, then in step 420 the account is frozen. Returning to step 400, if the ip address is recognized as being associated with the user, then in step 402 a username and a single level of password log-in is required. In step 412 a determination is made as to whether or not the password is valid. If a valid password, then the process proceeds to step 424. If not, then in step 404 a determination is made as to the number of invalid attempts. After three invalid attempts, in step 406 the account is frozen and in step 408 an email is sent to the individual who may, in step 410, implement procedures to change the password and re-open the account.

Returning to step 424, a determination is made as to whether the account is associated with an individual or a family. If the account is associated with a family, then in step 426, the user can select the family member and access the family database 428. If, in step 424 the account is not a family account, then in step 430 the user can view their mailbox showing new PDF files and voice files. Preferably, these new files include date and time stamps so that the user can see when the files were received.

In step 432, the user is allowed to annotate the messages to better identify the messages in a manner that is convenient for the user. In step 434, the user can play the voicemail messages. In step 436, the user can choose to save the messages to voice storage 438 or to send the message to the trash 440. In step 442, the user can select a doctor to associate with the voicemail messages. For example, the doctor from which the voicemail or imaged document was received. Preferably the doctor is within the doctor database 444. If not, then in step 460, the user can update the doctor database 444 to include the doctor. The user can then organize the voicemail or document according to the user's preference into one or more file folders. Examples of file folders include RX 446, XRAYS 448, LABS 450, EXAM NOTES 452, OTHER 454. The user can make new file folders such as file folder 456 and identify it appropriately. The user interface offers functions 458 such as movement of files between folders, drag and drop, cut and paste, and/or other functions that will assist the user in organizing their records.

Figure 7:
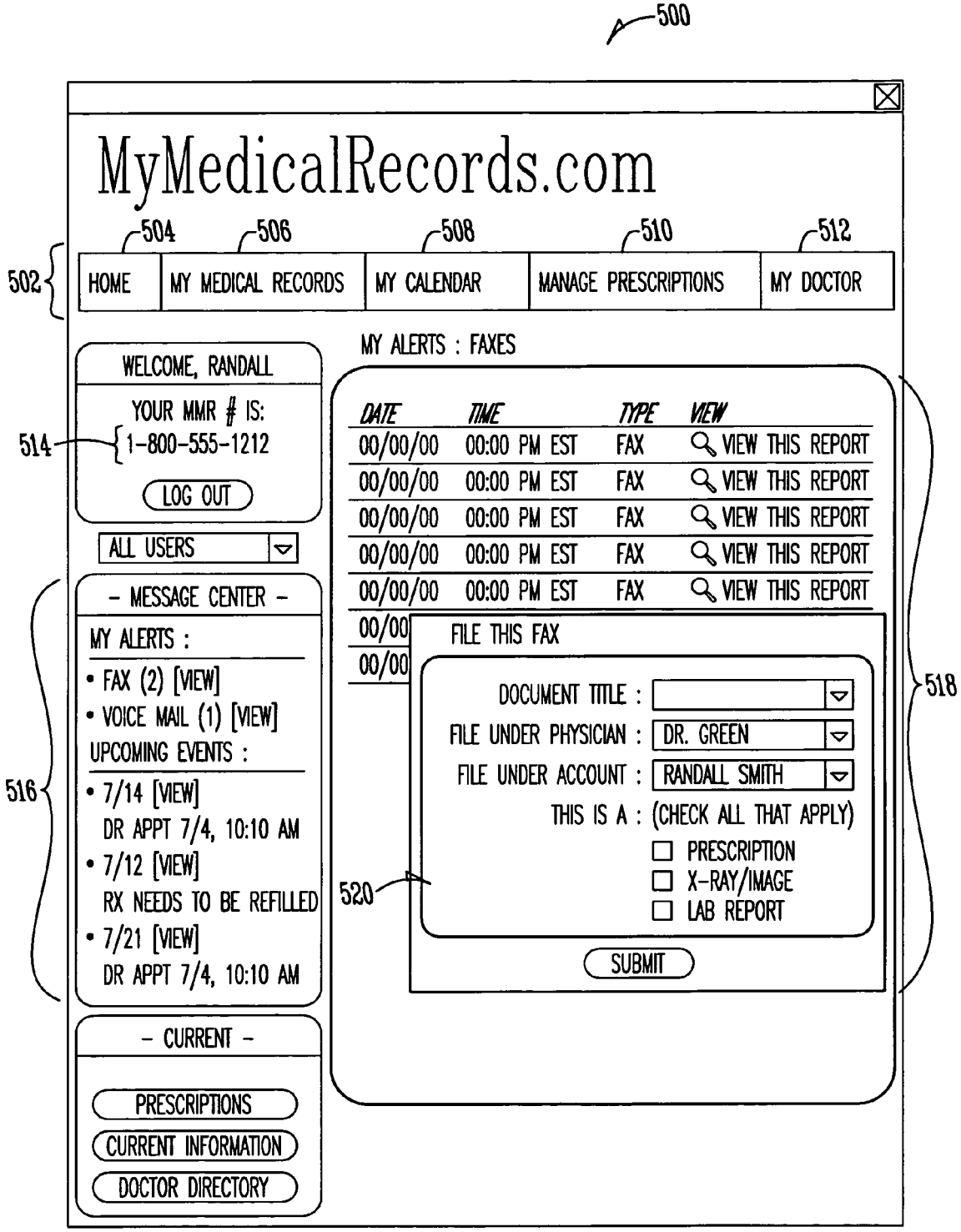
FIG. 7 is a screen display of a web site according to one embodiment of the present invention.

FIG. 7 illustrates one embodiment of a screen display of the present invention. In FIG. 7, the screen display 500 includes a menu bar 502 along the top with different menu items such as "Home" 504, "My Medical Records" 506, "My Calendar" 508, "Manage Prescriptions" 510 and "My Doctor" 512. The screen display 500 also includes a reminder to the individual of their LIFELINE toll free dedicated phone number 514. A message center 516 includes alerts as to recent faxes, voicemails, doctor appointments, prescription refills, or other related events. The user can view the recent faxes 518, and for each fax, can file it using fax filing options 520 which allow the user to give a document title to the fax, associate a physician with the fax, file the fax under a particular account where the account is a family account, and identify the fax as a prescription, x-ray/image, or lab report.

Figure 8:
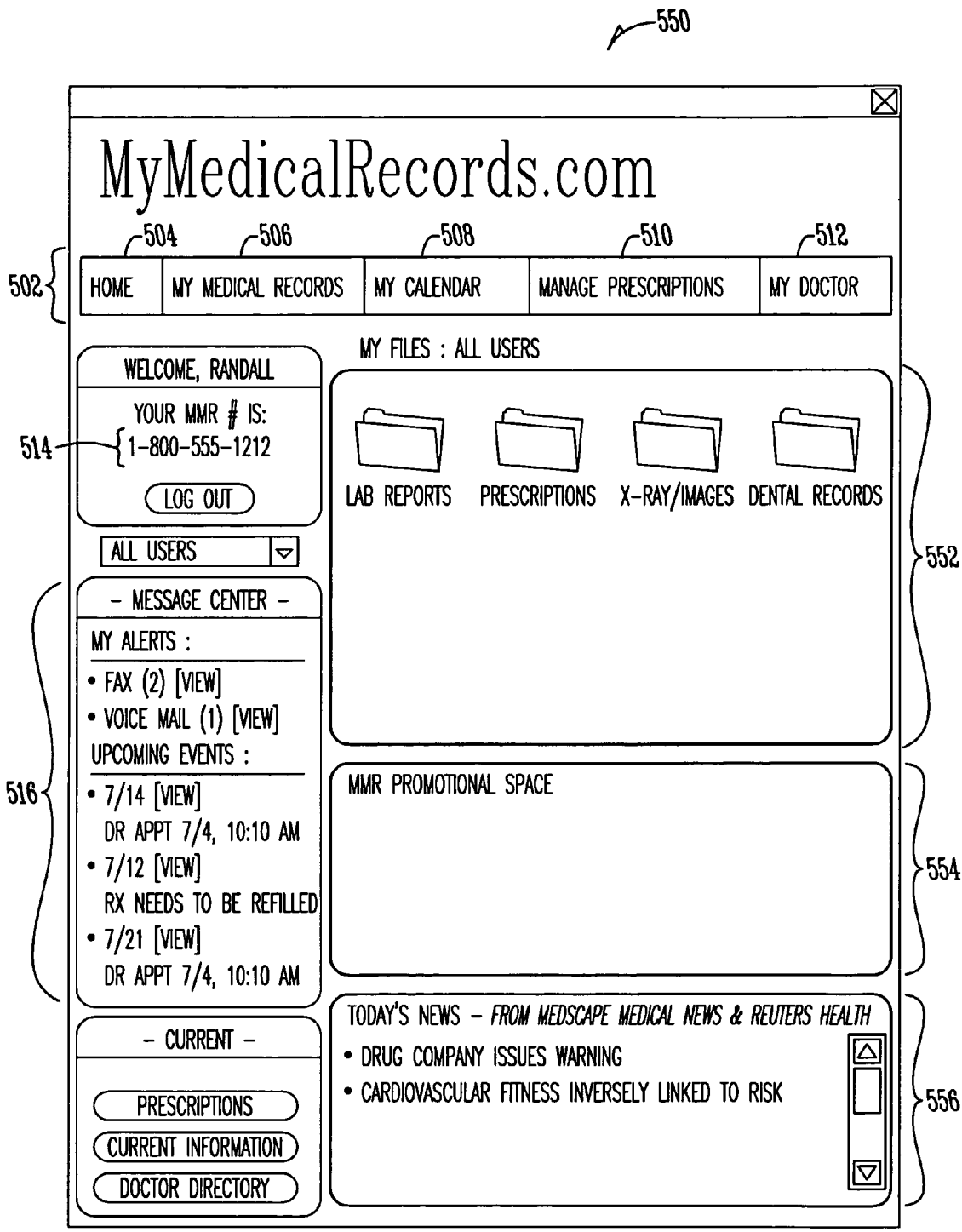
FIG. 8 is another screen display of a web site according to one embodiment of the present invention.

FIG. 8 illustrates another example of a screen display according to one embodiment of the present invention. In FIG. 8, the screen display 550 also includes a files section 552 wherein different folders are shown for storing and organizing information. This allows a user to store records in a manner appropriate for them. In one embodiment, the folders can include separate folders for lab reports, prescriptions, x-ray/images, dental records, lab reports, prescriptions, and all records. As shown in FIG. 8, there is a promotional space 554. The present invention allows for promotional material to be placed in the promotional space 554 that is of potential interest to the user. The promotional information can come from a third party source or advertiser. In additions, news information may be placed in a news information portion 556 of the web page. The news information can include breaking news regarding the medications that the patient is on, health and fitness news, or other news of potential interest or importance to the user.

Figure 9:
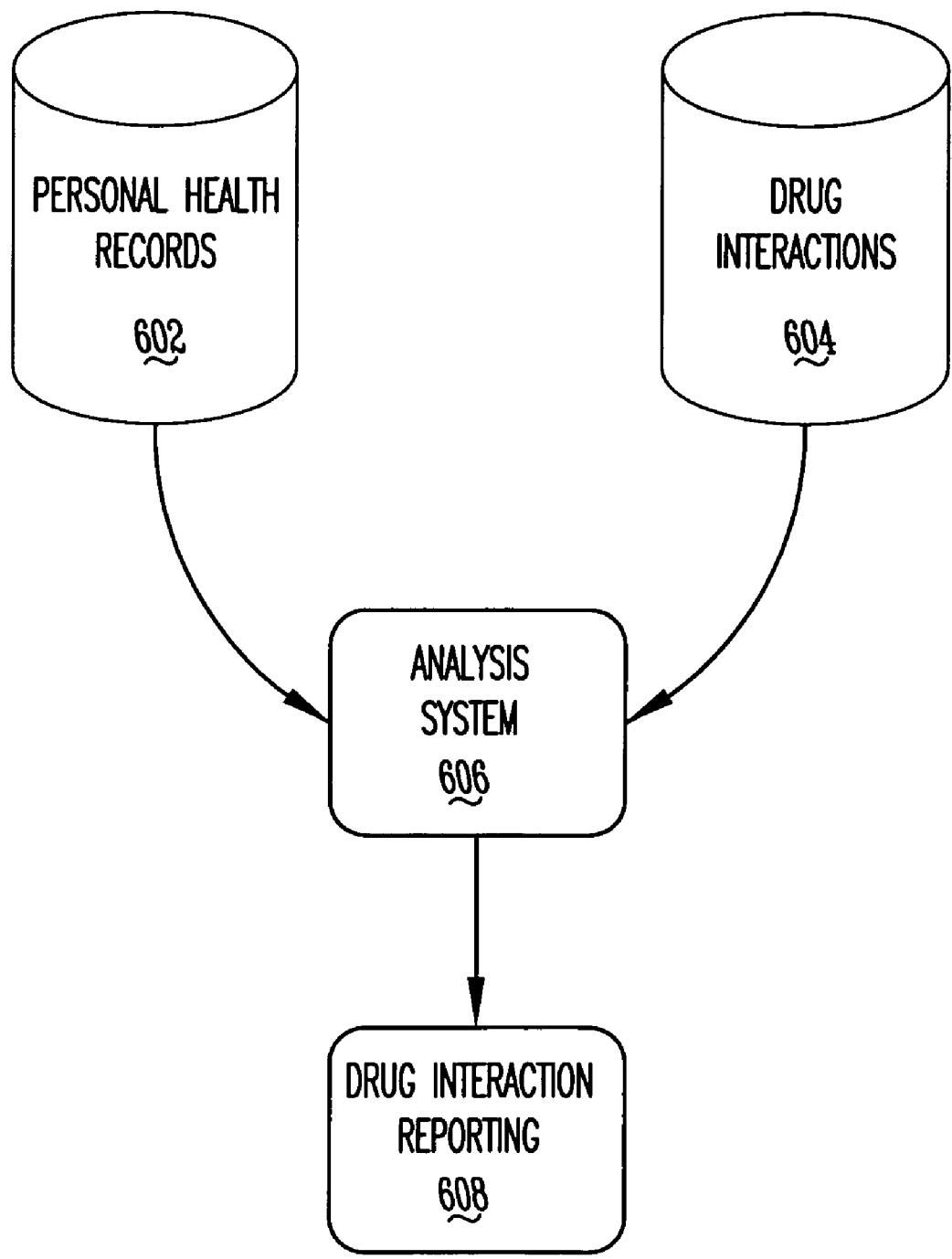
FIG. 9 is diagram illustrating one embodiment of drug interacting reporting and analysis of the present invention.

FIG. 9 illustrates one embodiment of using the health-related information collected to provide additional benefits to a consumer. For example, the present invention allows for a system 600 that includes a personal health records database 602 and a drug interactions database 604 operatively connected to an analysis system 606. The analysis system 606 is operatively connected to a drug interaction reporting component 608. The personal health records includes information regarding which prescription drugs are being taken by the user. The drug interactions database 604 includes information regarding known interactions between different drugs. The analysis system 606 analyzes the prescription drugs taken by the user to determine if there is any known interaction that may be adverse in any way to the user. Based on the results of this analysis, the drug interaction reporting component 608 reports the results to the user, their pharmacist, doctor, or other health care provider as appropriate. The present invention contemplates that drug interaction reporting can be reported in different ways to different people based on factors such as user preferences regarding the drug interacting reporting, the severity or certainty of a determined adverse drug interaction, or otherwise. The present invention contemplates that in addition to drug interaction analysis and reporting, other types of analysis and reporting can be performed on the personal health records. One of the advantages of the present invention is that it allows for a convenient method to build and maintain complete and up-to-date health records, thus allowing the personal health records to be analyzed in any number of ways.

The present invention provides for numerous other features and advantages. For example, the web site can provide reminders for doctor appointments, prescription refills, or other events through email reminders or text messaging reminders. In addition, the web site allows the user to select the option of sending information via fax to a care provider. For example, a user can fax a prescription to their pharmacy of choice. In addition, the user can fax their medical records received from one health care provider to another health care provider.

The present invention is not to be limited to the specific disclosure provide herein. The present invention contemplates numerous variations as may be appropriate in a particular context, environment, or situation. For example, the present invention contemplates that the health care records can be medical records or dental records. The present invention contemplates that the health care records can include records for pets as well as humans, and other variations.

What is claimed is:

1. A method for providing a consumer with a service to access and collect personal health records associated with the consumer in a secure and private manner, comprising:
   providing a phone number to the consumer through a web site, the phone number individually associated with and dedicated to the consumer for private fax and voice communications from a health care provider;
   associating access information with the consumer for the consumer to use to access the web site hosted on a web server using a web-enabled device;
   providing the consumer with a document to provide to the health care provider, the document requesting and providing authorization from the consumer to the health care provider for faxing existing personal health records of the consumer to the phone number and faxing future personal health records of the consumer to the phone number as the future personal health records are created by the health care provider;
   receiving a private fax communication at a fax server, the private fax communication comprising a personal health record associated with the consumer for which the consumer has requested and authorized the health care provider to send to the phone number, wherein the personal health record is from the set consisting of a patient chart, a birth certificate, a vaccination record, a medical history, a lab report, a test result, a prescription, an x-ray result or image, a scan, and an EKG result or image;
   converting the private fax communications into an image file format at the fax server;
   storing the personal health record encoded in the image file format such that the personal health record is accessible through the web site;
   providing the consumer with access to the web site hosted on the web server, the access provided through use of the access information and providing on the web site an interface to the personal health records of the consumer for the consumer to use to access the personal health record;
   providing a means of receiving a voice communications message from the health care provider to the consumer and maintaining the voice communications message as private; and
   alerting the consumer of the voice communications message from the health care provider and providing the consumer with access information to access the voice communications message.

2. The method of claim 1 wherein the document is a sticker adapted for attachment to the personal health records.

3. The method of claim 1 further comprising providing the consumer with an emergency access card comprising the access information and adapted for use by a third-party to access the personal health record associated with the consumer in event of a medical emergency associated with the consumer.

4. The method of claim 1 wherein the web site interface further provides for organizing and annotating the personal health records by the consumer into separate file folders with functionality for the consumer to name the file folders and add file folders.

5. The method of claim 1 further comprising alerting the consumer of a fax transmission from the health care provider.

6. The method of claim 5 wherein the alerting comprises sending a text message.

7. The method of claim 5 wherein the alerting comprises sending an email.

8. The method of claim 5 wherein the alerting comprises sending a voice message.

9. The method of claim 1 further comprising providing on the web site means to calendar a prescription refill.

10. The method of claim 9 further comprising sending a reminder regarding the prescription refill.

11. The method of claim 1 further comprising providing on the web site means to calendar an appointment with a health care provider.

12. The method of claim 11 further comprising sending a reminder regarding the appointment with the health care provider.

13. The method of claim 12 wherein the reminder is a text message.

14. The method of claim 12 wherein the reminder is an email.

15. The method of claim 12 wherein the reminder is a voice message.

16. The method of claim 1 further comprising receiving payment from the consumer for facilitating access to the personal health records associated with the consumer.

17. The method of claim 1 wherein the web site provides means to facilitate creation of wallet cards containing access information and stickers requesting the health care provider to fax health records to the phone number.

18. The method of claim 1 wherein the health records include prescriptions for drugs and comprising analyzing interactions between the drugs and reporting the interactions.

19. A method for providing a user with a service to access and collect personal health records associated with the user in a private manner, comprising:
    assigning through a web site, a destination address associated with a user for private fax communications from a health care provider without having the health care provider enter a personal identification number of the user;
    associating access information with the user for the user to use to access a web site hosted on a web server using a web-enabled device;
    providing authorization to the health care provider to send existing and future personal health records to the destination address;
    receiving a private fax communication at a fax server, the private fax communication comprising a personal health record associated with the user for which the consumer has requested and given permission to the health care provider to send to a fax number;
    converting the personal health record into an image file format at the fax server;
    storing the personal health record encoded in the image file format such that the personal health record is accessible through the web site, wherein the personal health record is from the set consisting of a patient chart, a birth certificate, a vaccination record, a medical history, a lab report, a test result, a prescription, an x-ray result or image, a scan, and an EKG result or image;
    associating the personal health record encoded in the image file format with a user account of the user on the web site;
    providing the user with access to the user account on the web site through use of the access information;
    providing a means of receiving a voice communications message from the health care provider to the consumer and maintaining the voice communications message as private; and
    alerting the consumer of the voice communications message from the health care provider and providing the consumer with access information to access the voice communications message.

20. The method of claim 19 wherein the destination address identifies the user or the user account.

21. The method of claim 19 wherein the destination address comprises an individualized fax number.

22. A method for providing a user with functionality for accessing and collecting personal health records associated with the user, comprising:
    associating access information with the user for the user to use to access a web site hosted on a web server using a web-enabled device;
    providing the user with a document to provide to the health care provider, the document requesting and providing authorization from the user to a health care provider for faxing existing personal health records of the user to a phone number and faxing future personal health records of the user to the phone number as the future personal health records are created by the health care provider;
    receiving at the web site a personal health record encoded in an image file format, wherein the personal health record is from the set consisting of a patient chart, a birth certificate, a vaccination record, a medical history, a lab report, a test result, a prescription, an x-ray result or image, a scan, and an EKG result or image;
    associating the personal health record encoded in the image file format with a user account of the user on the web site;
    providing the user with access to the user account on the web site hosted on the web server, the access granted through use of the access information;
    providing a means of receiving a voice communications message from the health care provider to the consumer and maintaining the voice communications message as private; and
    alerting the consumer of the voice communications message from the health care provider and providing the consumer with access information to access the voice communications message;
    wherein the personal health record encoded in the image file format is a representation of a faxed communication from a health care provider directed to an individual phone number uniquely associated with the user account to thereby provide for conveniently collecting the personal health records from the health care provider.

23. The method of claim 22 wherein the individual phone number is a toll-free phone number.

24. A method for providing a user with functionality for accessing and collecting personal health care records associated with the user, comprising:
    associating access information with the user to use to access a web site hosted on a web server using a web-enabled device;
    providing the user with a document to provide to a health care provider, the document requesting and providing authorization from the user to the health care provider for faxing existing personal health records of the user to a phone number and faxing future personal health records of the user to the phone number as the future personal health records are created by the health care provider;
    receiving at the web site a personal health care record encoded in an image file format from the health care provider, wherein the personal health record is from the set consisting of a patient chart, a birth certificate, a vaccination record, a medical history, a lab report, a test result, a prescription, an x-ray result or image, a scan, and an EKG result or image;
    automatically determining a user account associated with the personal health care record and associating the personal health care record with the user account on the web site;
    providing the user with access to the user account on the web site through use of the access information;
    providing a means of receiving a voice communications message from the health care provider to the consumer and maintaining the voice communications message as private;
    alerting the consumer of the voice communications message from the health care provider and providing the consumer with access information to access the voice communications message;
    wherein the personal health care record encoded in the image file format is a representation of a faxed communication from the health care provider.

25. The method of claim 24 wherein the phone number is individually associated with and assigned to the user through the web site.

* * * * *

UNITED STATES PATENT AND TRADEMARK OFFICE
CERTIFICATE OF CORRECTION

| | | |
|---|---|---|
| PATENT NO. | : 8,121,855 B2 | |
| APPLICATION NO. | : 11/225518 | |
| DATED | : February 21, 2012 | |
| INVENTOR(S) | : Robert H. Lorsch | |

It is certified that error appears in the above-identified patent and that said Letters Patent is hereby corrected as shown below:

Column 13, Claim 17, Line 2:
ADD: after to fax --personal--

Column 13, Claim 18, Line 3:
ADD: after wherein the --personal--

Column 13, Claim 19, Line 21:
DELETE: "consumer"
ADD: --user--

Column 13, Claim 19, Line 39:
DELETE: "consumer"
ADD: --user--

Column 13, Claim 19, Line 42:
DELETE: "consumer"
ADD: --user--

Column 13, Claim 19, Line 44:
DELETE: "consumer"
ADD: --user--

Column 14, Claim 22, Line 10:
DELETE: "consumer"
ADD: --user--

Column 14, Claim 22, Line 13:
DELETE: "consumer"
ADD: --user--

Signed and Sealed this
Fourteenth Day of August, 2012

David J. Kappos
*Director of the United States Patent and Trademark Office*

Column 14, Claim 22, Line 15:
DELETE: "consumer"
ADD: --user--

Column 14, Claim 24, Line 53:
DELETE: "consumer"
ADD: --user--

Column 14, Claim 24, Line 56:
DELETE: "consumer"
ADD: --user--

Column 14, Claim 24, Line 58:
DELETE: "consumer"
ADD: --user--